(12) United States Patent
O'Donoghue (10) Patent No.: US 7,744,616 B2
(45) Date of Patent: Jun. 29, 2010

(54) SURGICAL SAGITTAL SAW BLADE WITH ANGLED TEETH AND CHIP CATCHMENT AND RECIPROCATING SAW BLADE WITH BROACHED TEETH

(75) Inventor: Denis A O'Donoghue, Killarney (IE)

(73) Assignee: Stryker Ireland, Ltd., Carrigtwohill (IE)

( * ) Notice: Subject to any disclaimer, the term of this patent is extended or adjusted under 35 U.S.C. 154(b) by 606 days.

(21) Appl. No.: 11/399,576

(22) Filed: Apr. 6, 2006

(65) Prior Publication Data

US 2007/0123893 A1 May 31, 2007

Related U.S. Application Data

(60) Provisional application No. 60/726,950, filed on Oct. 15, 2005.

(51) Int. Cl.
*A61B 17/14* (2006.01)
*A61B 17/32* (2006.01)
(52) U.S. Cl. .................... 606/177; 606/82; 606/86 R
(58) Field of Classification Search ......... 606/176–178, 606/82, 86 R; 30/339, 350, 278; 83/15, 83/835, 167–168, 848
See application file for complete search history.

(56) References Cited

U.S. PATENT DOCUMENTS

| | | | | | |
|---|---|---|---|---|---|
| 3,905,105 | A | * | 9/1975 | Tuke | 30/393 |
| 4,513,742 | A | * | 4/1985 | Arnegger | 606/178 |
| 5,087,261 | A | | 2/1992 | Ryd et al. | |
| 5,122,142 | A | * | 6/1992 | Pascaloff | 606/82 |
| 5,306,285 | A | * | 4/1994 | Miller et al. | 606/177 |
| 5,382,249 | A | * | 1/1995 | Fletcher | 606/79 |
| 5,403,318 | A | * | 4/1995 | Boehringer et al. | 606/82 |
| D361,029 | S | * | 8/1995 | Goris | D8/70 |
| 5,569,257 | A | * | 10/1996 | Arnegger et al. | 606/82 |
| 5,735,866 | A | * | 4/1998 | Adams et al. | 606/178 |
| 6,302,406 | B1 | * | 10/2001 | Ventura | 279/48 |
| 6,656,186 | B2 | * | 12/2003 | Meckel | 606/82 |
| 6,723,101 | B2 | * | 4/2004 | Fletcher et al. | 606/79 |
| 6,875,222 | B2 | * | 4/2005 | Long et al. | 606/172 |
| 7,001,403 | B2 | * | 2/2006 | Hausmann et al. | 606/178 |
| 2002/0116023 | A1 | | 8/2002 | Fletcher | |
| 2004/0098000 | A1 | * | 5/2004 | Kleinwaechter | 606/167 |

FOREIGN PATENT DOCUMENTS

DE      202 11 397 U1   10/2002

(Continued)

OTHER PUBLICATIONS

PCT App. No. PCT/IB/2006/002968, International Search Report, Apr. 2007.

(Continued)

*Primary Examiner*—Thomas C Barrett
*Assistant Examiner*—Larry E Waggle, Jr.

(57) ABSTRACT

A sagittal saw blade wherein the teeth are arranged so that relative to the teeth located closer to the outer sides of the blade, the inner located teeth are located closer to the proximal end of the blade. The blade is further formed to have an opening between at least two of the teeth that extends proximally rearward. The opening increases in width as the opening extends proximally along the length of the blade. The opening opens into a void space that functions as a chip catchment space.

20 Claims, 10 Drawing Sheets

FOREIGN PATENT DOCUMENTS

| | | |
|---|---|---|
| DE | 203 03 018 U1 | 4/2003 |
| EP | 0 695 607 A1 | 2/1996 |
| EP | 695607 A1 * | 2/1996 |
| EP | 0 695 607 B1 | 3/1999 |
| JP | 03 128050 A | 5/1991 |
| WO | 94/14438 A | 7/1994 |

OTHER PUBLICATIONS

PCT App. No. PCT/2006/002968 Written Opinion of the ISA, Apr. 2007.

* cited by examiner

FIG. 11 under 35 U.S.C. Sec. 119# SURGICAL SAGITTAL SAW BLADE WITH ANGLED TEETH AND CHIP CATCHMENT AND RECIPROCATING SAW BLADE WITH BROACHED TEETH

RELATIONSHIP TO EARLIER FILED APPLICATION

This application claims priority under 35 U.S.C. Sec. 119 from U.S. Patent Application No. 60/726,950 filed 15 Oct. 2005.

FIELD OF THE INVENTION

This invention relates generally to surgical saw blades. More particularly, this invention relates to a sagittal surgical saw blade that, when actuated, is relatively stable. This invention also relates to a surgical saw blade with a catchment for receiving bone chips formed by the blade. The invention also relates to a reciprocating surgical saw blade that efficiently cuts the tissue, bone, against which the blade is applied.

BACKGROUND OF THE INVENTION

In a surgical procedure, it is sometimes necessary to use a saw to remove tissue, including bone and cartilage. Often a powered saw is used to perform this procedure. Attached to the saw is a saw blade. A drive assembly internal to the saw reciprocates the blade in a back and forth motion. Some blades are constructed to pivot back and forth, oscillate, in the plane in which the blade is oriented. This type of blade is referred to as a sagittal saw blade. A sagittal saw blade is provided with teeth that extend forward from the distal end of the blade body. Other blades move back and forth along their longitudinal axes. This type of blade is known as a reciprocating saw blade. This type of blade is provided with teeth that extend outwardly from a side edge of the blade body.

Known varieties of both sagittal and reciprocating saw blades function reasonably well. Nevertheless, there are limitations associated with the known varieties of both these blades. In particular, when a sagittal saw blade is pressed against bone in a cutting procedure, the blade can become unstable. Also, an inevitable byproduct of bone sawing process is the production of bone chips. These chips can accumulate in the interstitial space between the distal end of the sagittal saw and the bone the saw is employed to cut. The presence of these chips reduces the cutting efficiency of the saw.

Further, reciprocating saw blades are similarly known to their own inefficiencies. This is especially true with regard to the rate at which the blade cuts into the bone against which it is applied.

SUMMARY OF THE INVENTION

This invention relates to new and useful saw blades. Specifically, this invention is related to a sagittal saw blade with teeth arranged so, from the opposing side edges of the blade, the teeth are disposed inwardly relative to each other. This feature of the saw blade of this invention reduces the kick generated by the blade each time the blade cuts against a section of bone. The reduction of kick increases blade stability.

The sagittal saw blade of this invention is further constructed so that the blade body defines a void space behind the blade teeth. The void space functions as a catchment into which the bone chips formed during the cutting process flow. Since the bone chips flow into the catchment, the chips do not build up in the space between the blade teeth and the bone being cut. The minimization of bone chip build up along this interface improves the cutting efficiency of the blade.

The reciprocating saw blade of this invention is designed so that the blade teeth are arranged in a pattern that is not parallel to longitudinal axis of the blade body. An advantage of the angled relationship of the blade teeth of this invention is that, during a single cutting motion, the later teeth cutting the bone are in a deeper position. This increases the amount of material these later teeth are able to remove. Thus, the tooth pattern of the reciprocating saw blade of this invention improves the cutting efficiency of the blade.

BRIEF DESCRIPTION OF THE DRAWINGS

The invention is pointed out with particularity in the claims. The above and further features and benefits of this invention are understood by reference to the following Detailed Description taken in conjunction with the accompanying drawings in which:

DETAILED DESCRIPTION

Figure 1:
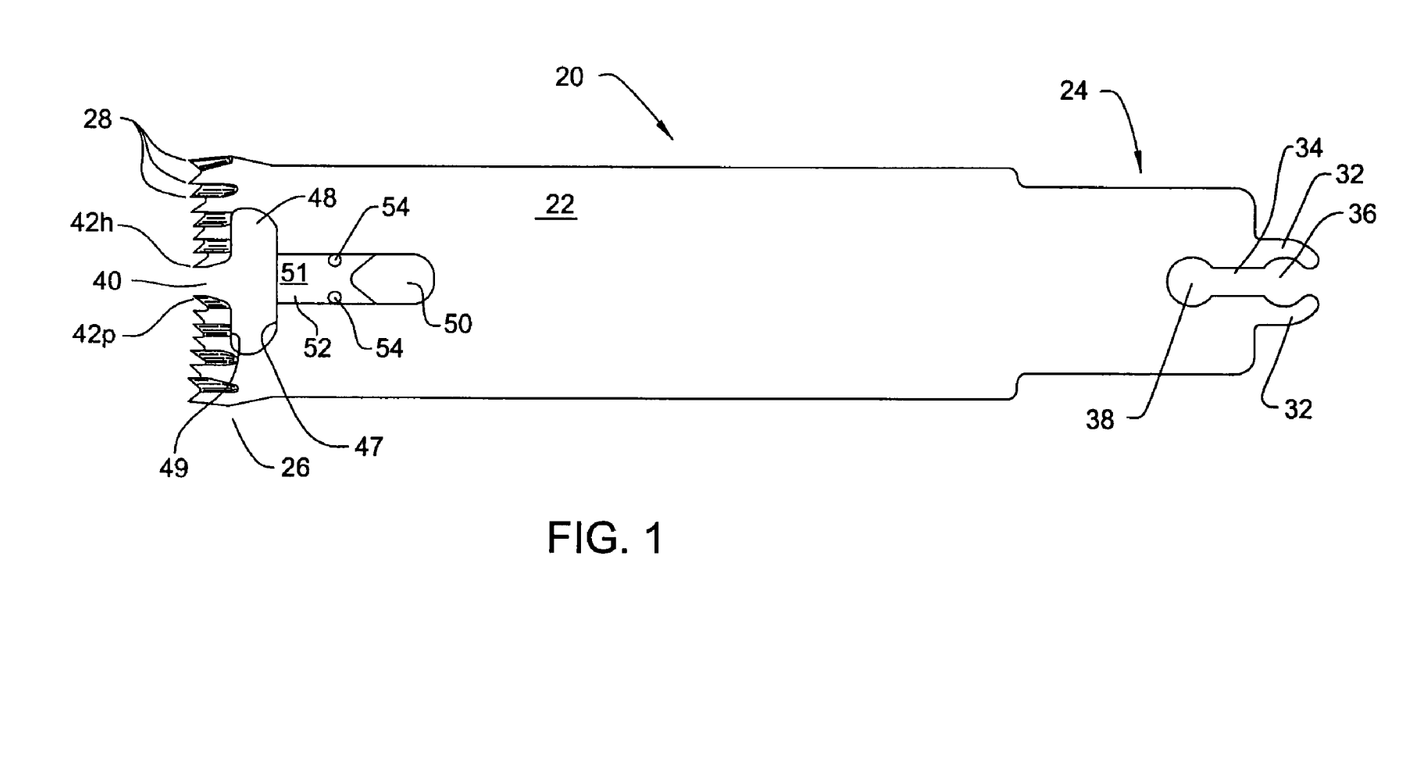
FIG. 1 is a plan view of a sagittal saw blade constructed in accordance with this invention.
Figure 2:
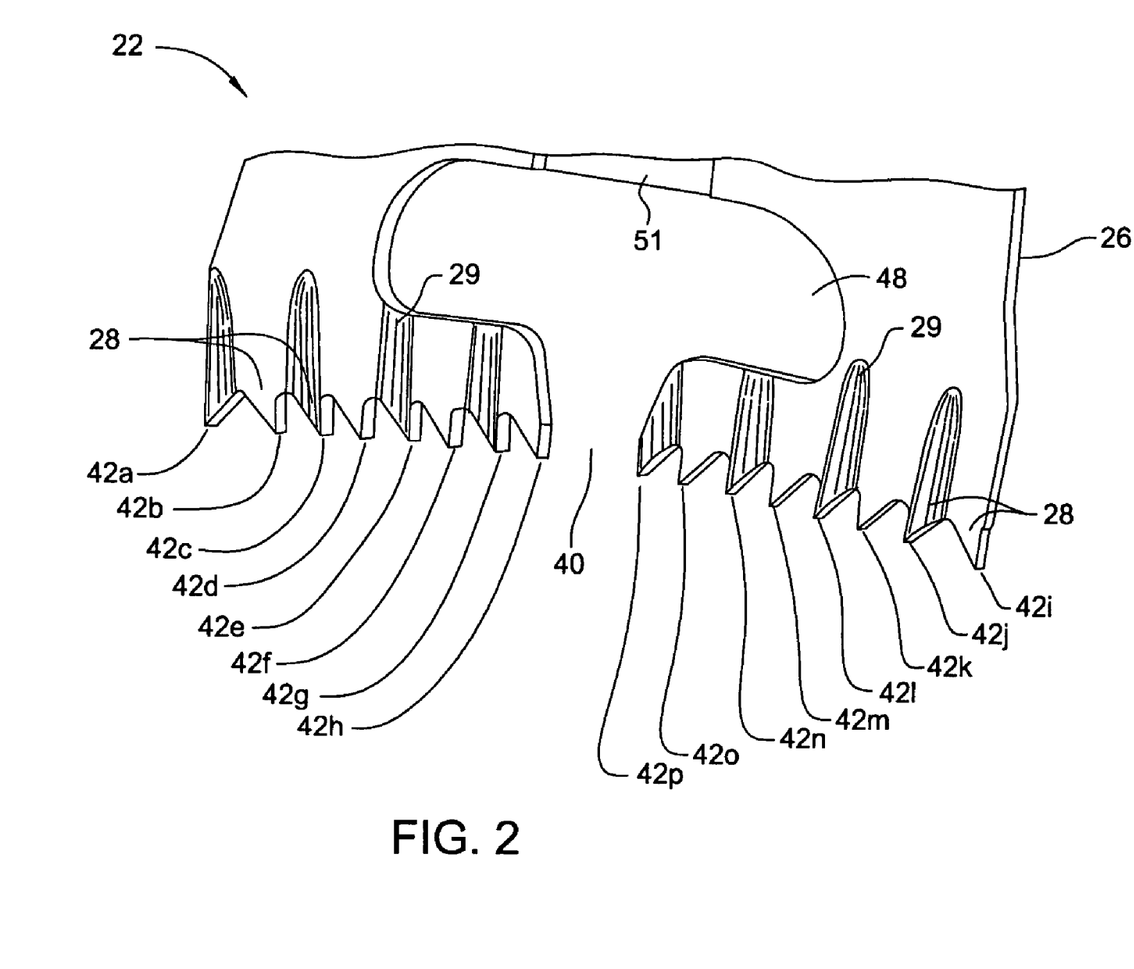
FIG. 2 is an enlarged perspective view of the distal end of the saw blade of FIG. 1.

FIGS. 1 and 2 illustrate a surgical sagittal saw blade 20 constructed in accordance with this invention. Blade 20 has a planar blade body 22 formed of material such as stainless steel. Blade body 22 has opposed proximal and distal ends 24 and 26, respectively. ("Proximal" it is understood means towards the surgeon, away from the surgical site to which the blade is applied. "Distal" means away from the surgeon, towards the surgical site.) The blade is formed so that teeth 28 extend forward from the blade body distal end 26. Not identified are cuts formed in the distal end of the body 22 as a consequence of the machining of the teeth.

The blade 20 is further formed so that the body proximal end 24 is formed with geometric features that facilitate the coupling of the blade to the saw drive head that oscillates the blade. Specifically, saw blade 20 is a sagittal blade. Thus, the proximal end geometric features facilitate the coupling of the blade to a drive head that oscillates the blade around an axis that extends through the plane in which the blade lies. In other words, blade distal 26 end pivots back and forth relative to proximal end 24.

In the illustrated blade 20, these features include: a pair of spaced apart tines 32 that extend rearwardly from the base proximal end 24; and a slot 34 that extends between the tines and into the blade body. The coupling geometric features of the illustrated blade 20 also include two openings 36 and 38 that intersect slot 34. Opening 36, the more proximal of the two openings, is partially formed by the tines 32. The distal of the two openings, opening 38, forms the terminus of slot 34 and extends through the body proximal end 24. It should be understood that the foregoing geometric features are merely illustrative of one set of geometric features saw 20 of this invention may have to facilitate its coupling to a drive head. The disclosed features should not be considered limiting. Still other possible, and again not limiting, geometric features are disclosed in U.S. Pat. No. 5,306,285, SURGICAL SAW BLADE, issued Apr. 26, 1994, the contents of which are incorporated herein by reference.

By reference to FIG. 2, the arrangement of the saw teeth 28 relative to the blade body 22 is now described. Each tooth 28 in the illustrated version of the invention is in the form of a right triangle. This particular type of tooth geometry is referred to as a "rake" tooth. Each tooth 28 is formed to have a most distal end tip, a point. In FIG. 2, going left to right from the left most tooth 28 to the tooth immediately to the left of the front end opening 40, the teeth individually define points 42a, b, c, . . . h. Going from right to left from right most tooth to the tooth immediately to the right of front end opening 40, the teeth individually define points 42i, j, k, l, m, n, o, and p.

The teeth 28 are arranged so that, on each side blade, each tooth relative to the adjacent more outwardly located tooth is located inwardly, closer to the blade body proximal end 24. Thus, teeth points 42b, c, d, e, f, g and h are, respectively, located inward of teeth points 42a, b, c, d, e, f and g. On the right side of the blade, teeth points 42j, k, l, m, n, o and p are located inward of teeth points 42i, j, k, l, m, n and o, respectively. In some versions of the invention, teeth 28 are arranged so that the opposed sets of teeth are arranged so that the teeth points 42a, b, c, d, e, f, g and h and 42i, j, k, l, m, n, o and p lie on symmetric lines or arcuate plots. Alternatively, all the teeth can be arranged so that all the tooth tip points 42a, b, c, . . . p lie on the same curve. It is appreciated that this curve extends inwardly, in a concave pattern, relative to the outer side edges of the distal end of the blade body.

It should be further understood that the outermost teeth 28, the teeth forming points 42a and 42i, have different geometries than the teeth immediately inward of these teeth, teeth forming points 42b and 42j, respectively. Specifically, the rake surfaces of these outer teeth are opposite in orientation than the rake surfaces of the immediately adjacent inner teeth. Thus, the rake surface of tooth forming point 42a and opposed teeth forming points 42j, k, l . . . p are in the same orientation. Similarly, the rake surfaces of the tooth forming point 42i and the opposed teeth forming points 42b, c, d . . . h are in the same orientation.

Blade body 22 is formed with indentions, dubs 29, that extend rearwardly from teeth 28. The dubs 29 are spaced apart from each other. Dubs 29 are located on both sides of opening 40. On both sides of opening 40, plural dubs 29 are spaced laterally away from the opening 29. The outer most dubs taper into the planar surfaces of the blade body 22. The inner most dubs 29 similar taper such that their depth, relative to the planar surface of the blade body 22 decrease along the length of the blade body. The inner most dubs open into void space 48.

Since teeth 28 of this invention are, relative to the outer side edges of the blade, stepped inwardly, when the blade distal end 26 is applied against bone in a cutting action, at any given instant, only a few of teeth actually abut the bone. More particularly, as the blade 20 moves in one direction, sweeps to the left in FIG. 2, the tooth forming point 42a initially strikes the bone. For any one sweep, the rake surface of the tooth forming point 42a removes approximately 45% of the bone that is removed during the sweep. This tooth 28 also pushes the bone chips formed as a consequence of the cutting process away from the bone. Immediately thereafter, the teeth 28 forming points 42b through h move past the bone but do not cut the bone.

Then, as the blade continues this sweep, the rake surfaces of teeth 28 forming points 42j through p remove the remaining layer of the bone material against which the blade is pressed in that sweep. Specifically, in this portion of the sweep, the tooth forming point 42p starts the cutting process and the teeth forming points 42o, n, m through j complete the cutting in that sequence. Also in this process, the teeth forming points 42j through p push the bone chips to the center of the oscillating arc of the blade so the chips flow into the opening 40. The teeth 28 forming these points 42j through p, also push the bone chips out through the adjacent dubs 29 formed in the blade body that extend proximally away from the teeth.

In the opposed sweep, the blade moves to the right in FIG. 2, the tooth forming point 42i performs the initial bone removal function. The teeth forming points 42b through h perform the additional bone removal cutting and chip removal of this sweep.

An inevitable result of a blade tooth abutting bone is the transmission of force from the edge of the tooth downline towards the blade body proximal end 24. In this invention, since only a few teeth simultaneously strike the bone, in comparison to convention teeth arranged in a straight line, there is only a relatively small force generated at any given instant. The reduction in the instantaneous generation of this back force, sometimes referred to as "kick," reduces the extent to which the blade 20, when used, vibrates. The lessening of this vibration increases the overall stability of the blade.

Blade 20 of this invention is further formed to have the front end opening 40. Opening 40 is centered on the longitudinal axis of and extends through the blade body 22 from proximal end 24 to distal end 26. The front end opening 40, which opens rearwardly from the distal end of the blade, separates the tooth 28 forming point 42h with the tooth forming point 42p. Saw blade 20 is further formed so that extending proximally rearward from the outer distal end of the blade, the front end opening 40 has an increasing width.

Extending proximally rearward along the blade body 22, front end opening 40 opens into a first void space 48 also extending through the body 22. The first void space 48 has an elongated shape and positioned to have a longitudinal axis that is perpendicular to the longitudinal axis of the blade body 22. More particularly, the length of void space 48 of blade 20 of FIGS. 1 and 2 along the longitudinal axis of the void space is at least that of the combined width of opening 40 and the widths of a plurality of teeth 28 on both sides of the opening. The blade 20 is further formed so that at on either side of the opening at least one of the dubs 29 spaced laterally away from opening 40, opens into void space 48. Blade 20 is further shaped so that proximal edge 47 of the first void space 48 in the body is of shorter length than the opposed distal edge 49.

Blade 20 also is formed with a second void space 50 that is proximally spaced apart from the first void space 48. In the version of the blade depicted in FIG. 1, second void space has generally an oval shape such that it has a longitudinal axis that extends over the longitudinal axis of the blade boy 22. The distal end of the second opening has a pointed shape. First and second void spaces 48 and 50, respectively, are separated by a web 51 centered along the longitudinal axis of the blade body 22.

Web 51 has a thickness less than that of the associated blade body 22. Thus, the web 51 defines a recess 52 in the blade body 22 that extends between first void space 48 and second void space 50. In actuality, the blade 20 is formed so that the center plane through the web 51 is coplanar with the center plane through the blade body 22. Accordingly, while not illustrated, it should be understood the blade is formed with two recesses 52 on opposed sides of the blade body 22. In the illustrated versions of the invention, web 51 and recesses 52 have the same width as the second void space 50. This is not a requirement for all versions of the invention.

Two diametrically opposed supplemental openings 54 are also formed in the blade body 22 between the first and second void spaces 48 and 50. Openings 54 extend through web 51 to reduce weight and, therefore, vibration.

When sagittal saw blade 20 of this invention is actuated and pressed against bone, the teeth 28 cut the bone and form bone chips. The bone chips flow through the front end opening 40 into first void space 48. Owing to the profile of the front end opening, the opening widens extending proximal from teeth 28; there is little likelihood the bone chips will become trapped in the opening. In the event the bone chips substantially fill the first void space 48, the most distal located chips are pushed distally through recesses 52 into the second void space 50. For many procedures in which saw blade 20 is used, second void space 50 is spaced relatively far from the surgical site to which the teeth 28 are applied. Often this distance is between 2 and 9 cm away from teeth 28. Consequently, should void space 50 fill with bone chips, the chips are ejected proximally rearwardly without adversely affecting the surgical procedure.

Front end opening 40 functions as a discharge conduit for bone chips generated during the bone sawing process. Void spaces 48 and 50 function as catchments for containing the discharged bone chips. Thus, when saw blade 20 of this invention is actuated, at any given instant, there is only a small layer of bone chips between the blade teeth 28 and the bone. Since this bone chip layer is relatively narrow, if present at all, there are few chips present to reduce the efficiency of the cutting process.

Figure 3:
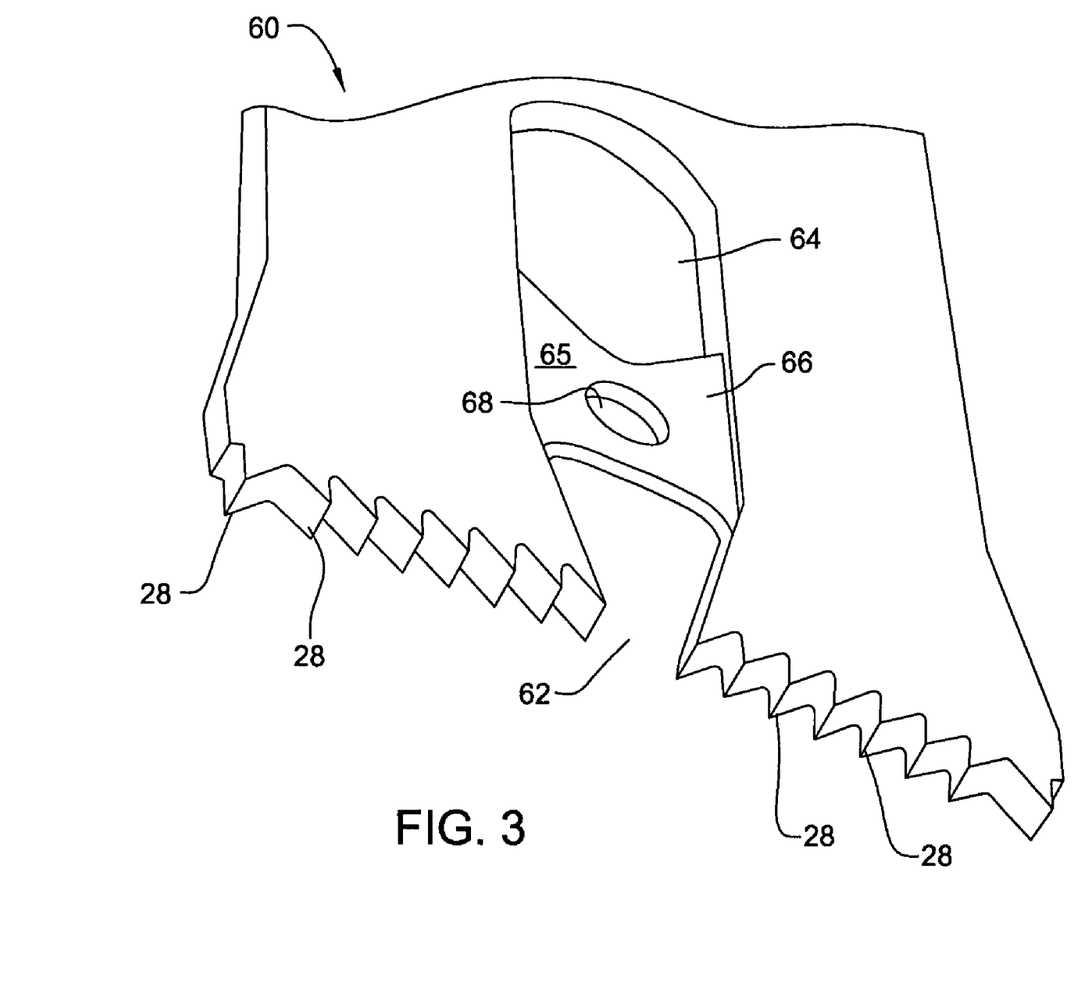
FIG. 3 is a perspective view of distal end of an alternative sagittal saw blade of this invention.

FIG. 3 illustrates the distal end of an alternative sagittal saw blade 60 of this invention. Blade 60 has the same teeth 28 and teeth pattern of the blade of FIGS. 1 and 2. Blade 60 is further formed to have a front end opening 62. Front end opening 62 has a triangular shape such that the narrow portion of the opening is at the distal end of the blade and the wide portion is located proximal to the teeth 28. A void space 64 is located rearwardly and spaced from opening 62. Void space 64 has the same geometric profile as the second void space 50 of blade 20.

A web 65 separates front end opening 62 and void space 64. Web 65 has a thickness less than that of the blade body with which the web is integral. Web 65 thus defines two opposed recesses 66 (one shown) on the opposed planar surfaces of the blade body. Each recess 66 extends between the proximal end of front end opening 62 and the distal end of void space 64. A circularly shaped opening 68 extends through web 65 for weight and vibration reduction purposes.

Figure 4:
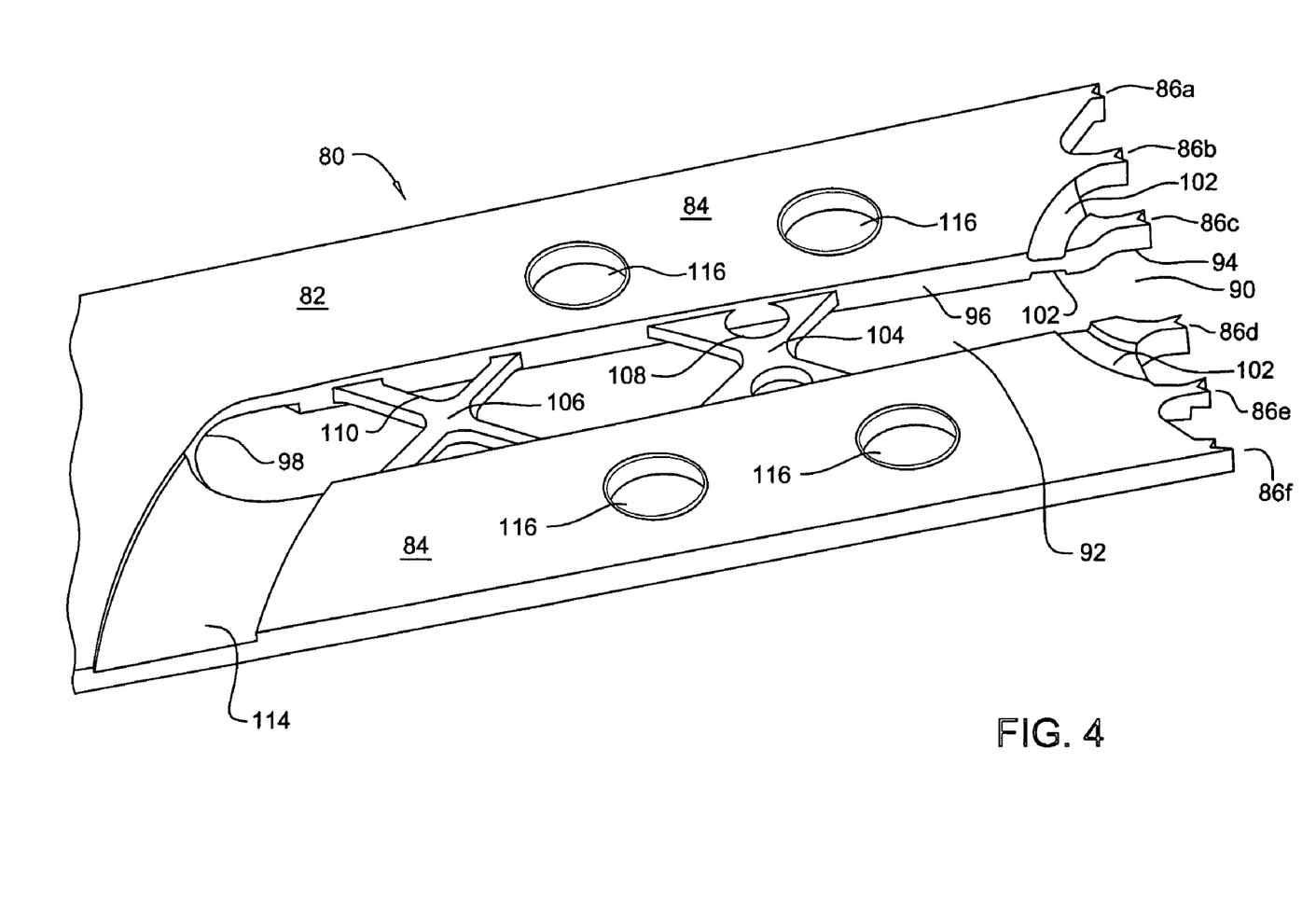
FIG. 4 is a perspective view of distal end of a second alternative sagittal saw blade of this invention.

FIG. 4 illustrates the distal end of a second alternative sagittal saw blade 80 constructed in accordance with this invention. Blade 80 has a body 82 shaped to have two spaced-apart tines 84. Tines 84 are positioned symmetrically around the longitudinal axis of the blade body 82. Teeth 86 extend forward from the distal ends of the tines 84. In this particular version of the invention, teeth 86 are positively raked teeth. It should be recognized that this is solely for the purposes if illustration, the invention is not so limited.

Blade tines 84 are shaped so as to form therebetween both a front end opening 90 and a void space 92. More particularly, front end opening 90 is formed by opposed side surfaces of teeth 86c and 86d and inner side wall sections 94 of the tines (one tine inner side wall section 94 identified). The inner side wall sections curve inwardly so as to provide the proximal end of front end opening the same cross sectional profile.

The narrowest section of front end opening 90 opens into void space 92. Void space 92 is defined by symmetrically opposed side wall sections 96 of the tines that extend proximally from sections 94. Blade body 82 is shaped so that extending proximally from the narrow width proximal end of the front end opening 90, void space 92 gradually widens. Proximally rearward of web 104, void space 92 has a constant width. Blade body 82 is further shaped so that the proximal end of the void space 92 is defined by a generally U-shaped surface 98 that extends between the tines 84.

Blade 80 is further shaped to define grooves 102 that extend from the distal ends of the tines 84 to the proximal end of void space 92. Each groove 102 extends from an open end surface of the tine 84 between the spaced apart rake surfaces of two adjacent teeth 86. The proximal end of each groove 102 opens into the void space 92 immediately rearward of the proximal narrow end of the front end opening 90. In the illustrated version of the invention, grooves 102 have a curved profile. More particularly, in this version of the invention, the angle between the distal front end opening of a groove and the opposed proximal end opening is between approximately 80 and 90°. The blade 80 is formed so that grooves 102 are formed on the opposed sides of the tines 84.

Two webs 104 and 106 extend between the tines 84 through void space 92. Both webs 104 and 106 are generally X-shaped. Web 104, the more distal of the two webs, is further shaped so that the opposed arms adjacent one tine form a circular opening 108. Web 106, the proximal-located web, is shaped so that opposed arms on each side of the web and the adjacent tine define a triangle shaped opening 110.

Both webs 104 and 106 are shaped to have a thickness less than that of the adjacent tines 84. The webs 104 are located on the blade so as to be inwardly recessed from the opposed planar outer surfaces of the blade body 82.

Blade 80 is further formed so as to define along at least one face a discharge slot 114. Discharge slot 114 is formed in the planar face of the blade body and extends from the proximal end base of the void space 92 to a side edge of the blade body 82. The blade is formed so that, extending away from the blade void space 92, discharge slot 114 curves proximally away from the void space.

Two circular openings 116 are further formed in each blade tine 84. Each opening 116 is symmetric with respect to a second opening 116 on the opposed tine 84. Openings 116 are provided to reduce weight and vibration.

Blade 80 of this invention is used in the same manner in which a conventional sagittal saw blade is used. During use of blade 80, some bone chips are forced through front end opening 90 into void space 92. Still other bone chips are pushed through grooves 102 into void space 92. Grooves 102 open into void space 92, not the front end opening 90. Therefore, the discharge of bone chips into the void space 92 from the grooves 102 does not impede the simultaneous discharge of chips into the void space from the front end opening 90.

During the course of the procedure, void space 92 may fill with bone chips and other material discharged from the surgical site. In this event occurs, material is ejected from void space 92 through discharge slot 114. In many versions of the invention, the side located opening of the discharge slot 114 is located at least 2 cm and more often 4 cm or more away from the distal end of the blade. This location is typically spaced from the surgical site at which the procedure is being performed. Consequently, the steps required to remove the material discharged from slot 114 does not appreciably further complicate the performance of the surgical procedure.

Figure 5:
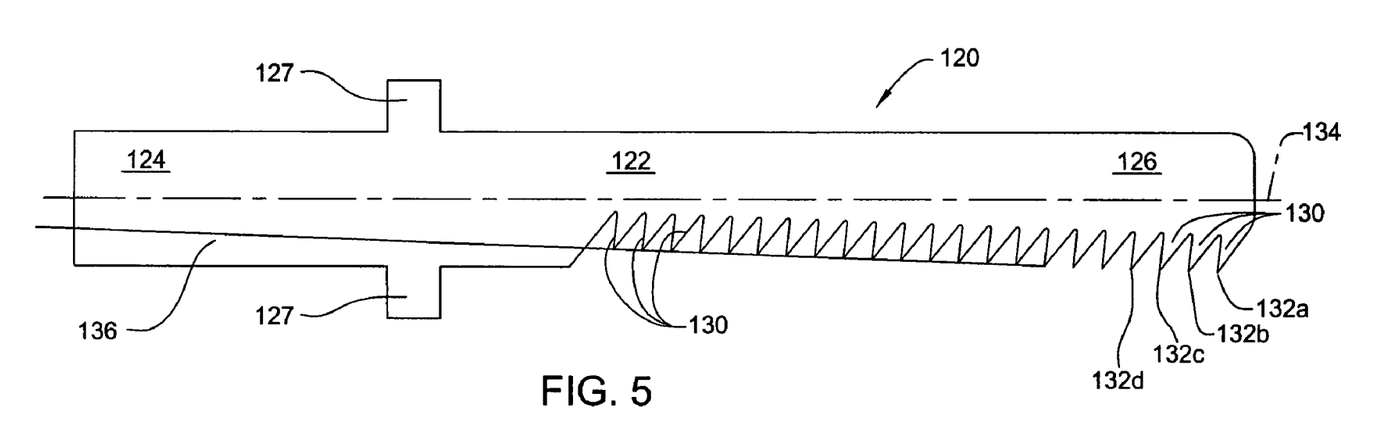
FIG. 5 is a plan view of a reciprocating saw blade, in particular a sternum saw blade, of this invention.

A reciprocating saw blade 120 of this invention is now described by reference to FIG. 5. The particular reciprocating saw blade is designed for use in a sternum saw. The Applicant's Assignee's U.S. Pat. No. 6,001,115, BLADE GUARD FOR A SURGICAL TOOL, issued 14 Dec. 1999, the contents of which are incorporated herein by reference, provides a discussion of the use of a sternum saw and complementary saw blade. It should be understood that the reciprocating saw blade of this invention is not limited to a sternum saw blade.

Saw blade 120 has a planar blade body 122 with opposed proximal and distal ends 124 and 126, respectively. Adjacent proximal end 124, blade body 122 is formed with geometric features that couple the body to a saw drive mechanism that reciprocates the blade. In the illustrated version of the invention, opposed tabs 127 that project laterally away from the side edges function as the geometric features. Again, it should be understood that the illustrated features are exemplary, not limited. In some versions of the invention, openings or notches formed in the blade body 122 function as the geometric features that facilitate the coupling of the blade to a drive mechanism.

Teeth 130 extend laterally outward from one side edge of blade 120. In the illustrated version of the invention, each tooth 130 is in the form of a triangle. Each tooth has an outer point, the outer points 132a, b, c and d of the four most distal teeth 130 are identified.

Reciprocating saw blade 120 of this invention is constructed so that teeth are positioned such that they are not aligned in a line parallel to the longitudinal axis of the blade body 122. For ease of reference, line 134 represents the longitudinal axis of the blade body. Instead the teeth 130 are arranged in a pattern so that proximal located teeth are closer to the blade longitudinal axis than the distal located teeth. Blade 120 is constructed so that teeth tips points 132b, c and d are closer to the longitudinal axis than the distally adjacent points, respectively tip points 132a, b and c. In this particular version of the invention, the teeth are arranged so that the teeth points 132 are on a line, line 136. Line 136 is angled relative to blade axis 134. In some versions of the invention, this angle is between 1 and 9°.

Saw blade 80 of this invention is used in manner essentially identical to the manner in which a conventional reciprocating/sternum saw blade is used. The blade 120 moves back and forth along the longitudinal axis 134. Owing to the broach angle, the angle between the teeth 130 relative to the longitudinal axis, at any one time all the teeth do not engage the cut line, the surface of the bone that is being cut. Consequently, teeth 130 cut deeper into the bone than teeth on a conventional blade.

Figure 6:
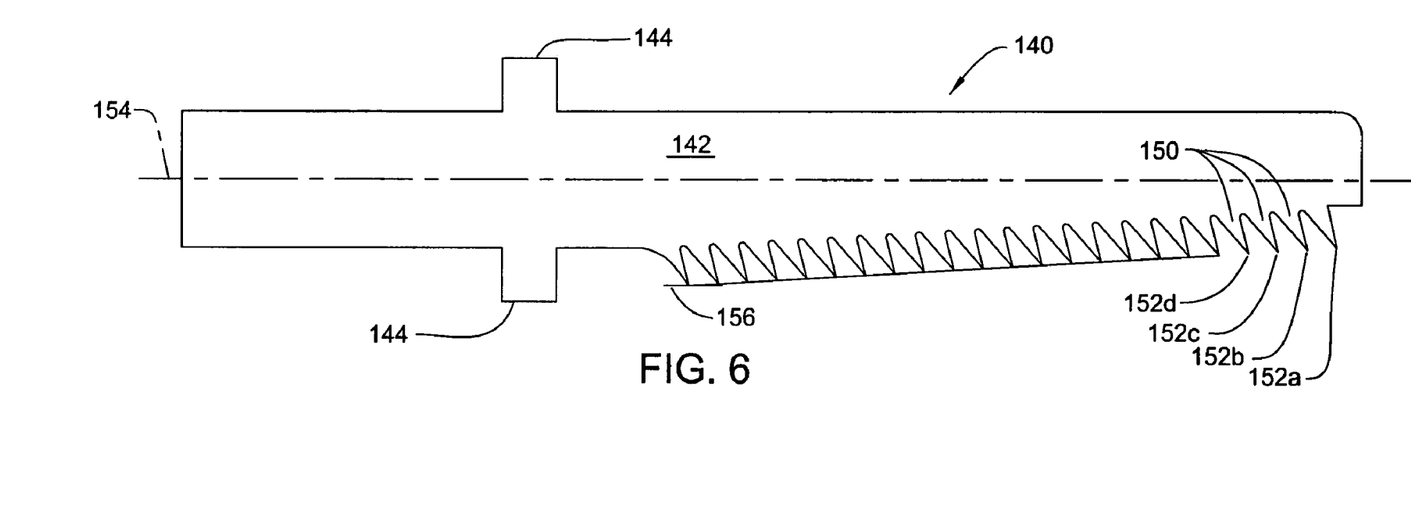
FIG. 6 is a plan view of an alternative version of the reciprocating saw blade of this invention.

FIG. 6 illustrates an alternative reciprocating saw blade 140 of this invention. Blade 140 has a body 142 with geometric features 144 identical to tabs 127 (FIG. 5) for holding the blade to the drive head that reciprocates the blade.

Saw blade 140 has teeth 150 each with a geometric profile similar to that of a tooth 90. Each tooth 150 thus has a point 152 that is the tip end of the tooth furthest spaced from longitudinal axis of the blade body 142. In FIG. 6, the four most distal teeth points 152a, b, c and d are identified. Line 154 represents the longitudinal axis of the blade.

Blade teeth 150 are arranged so as to be along a plot that is not parallel to the blade longitudinal axis 154. Instead, blade 140 is constructed so that teeth points 152b, c and d are further from the longitudinal axis than the distally adjacent points, respectively points 152a, b and c. In this particular version of the invention, the teeth 150 are arranged so that the teeth points 152 are on a line, line 156. Line 156 is angled relative to blade axis 154. In some versions of the invention, this angle is between 1 and 9°.

It should be appreciated the above description is directed to particular versions of this invention. Other versions of the invention may have features different from what has been described. For example, there is no requirement that this invention be restricted to blades having the illustrated teeth geometries. Blades of this invention can formed with teeth that have alternative geometries such as V-cut, rip, ground, negative rake, positive rake, or tooth set.

Likewise, as depicted in FIGS. 7-10, the bodies of the blades of this invention may be formed so as to have chip catchments with alternative geometries. The blade 160 of FIG. 7 has a blade body 162 that defines a single catchment-functioning void space 164. Specifically, blade 160 is formed to have two sets of teeth 166 that extend forward from the distal end of body 162. Between the two sets of teeth 166, body 162 has an opening 168. Opening 168 is centered along the longitudinal center axis of the blade 160. Blade body 162 is shaped so that extending from the distal front end of the opening 168, the end defined by the points of the surrounding teeth 166, the width of the opening increases. Blade 160, like blade 20, is further formed so that, on the opposed sides of opening 168, there are plural spaced apart dubs 167 formed in the teeth 166. On each side of the opening 168 there are plural dubs 167 spaced away from the opening.

Figure 7:
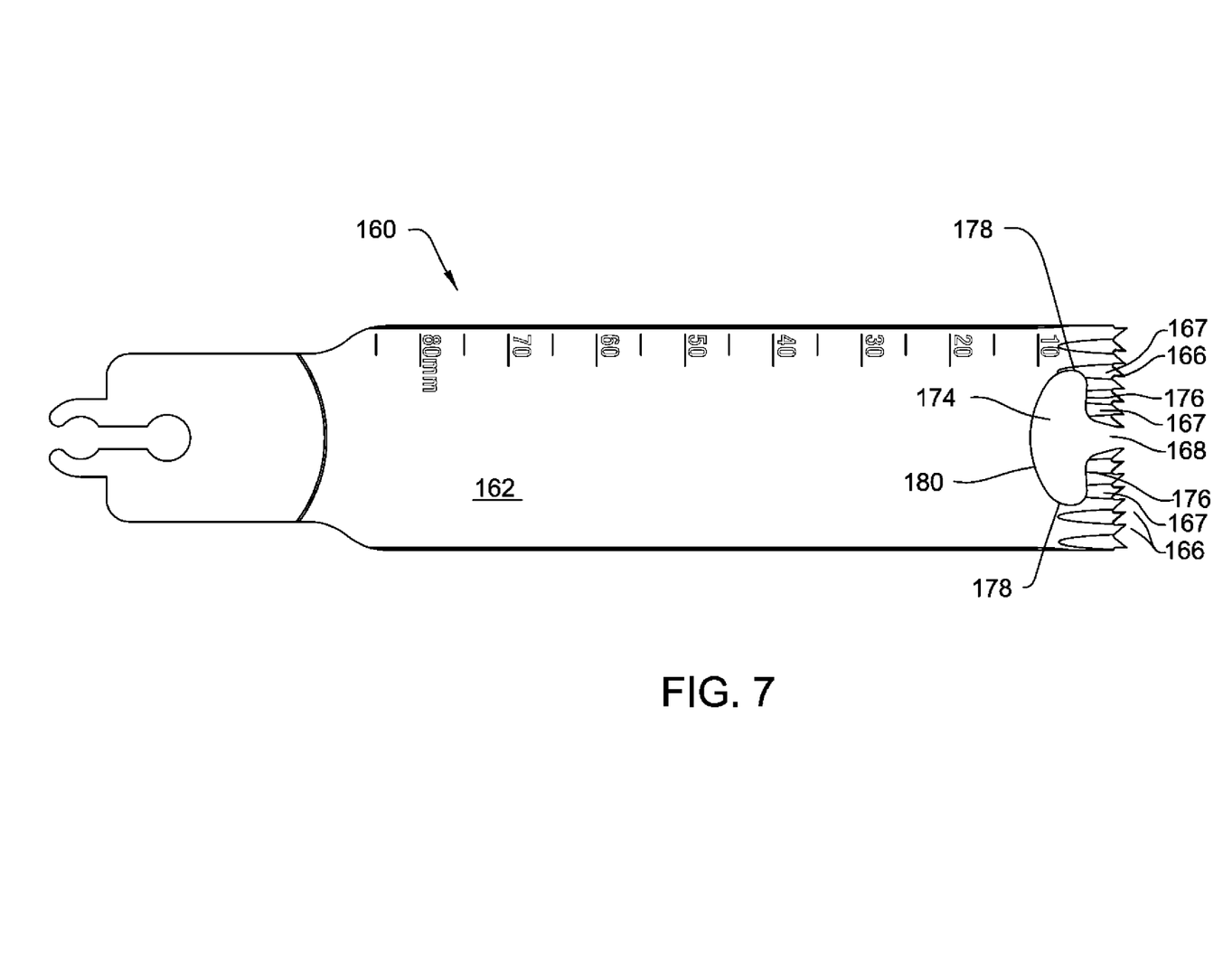
FIG. 7 is a plan view of a third alternative sagittal saw blade constructed in accordance with this invention.

Opening 168 opens into void space 174. Blade body 162 is formed so that opening 168 has a generally curved outer perimeter. Blade 160 is further formed so that void space 174 has a length perpendicular to the longitudinal axis of the blade that is at least equal to the width of opening 168 and the widths of a plurality of teeth on either side of the opening. This width is such that at least the dubs 167 on the opposed sides of the opening that are spaced from the opening 168 open into void space 174. Adjacent the location where opening 168 opens into the void space 174, the blade body 162 is shaped so that void space 174 has edges 176 that curve a slight distance forward of opening 168 on either side of the opening 168. Blade body 162 is further formed so that ends of the void space, the perimeter edges 178 perpendicular to the longitudinal axis of body 162, curve proximally rearward. The edge surface that defines the proximal end perimeter 180 of the void space 174 is also curved.

Figure 8:
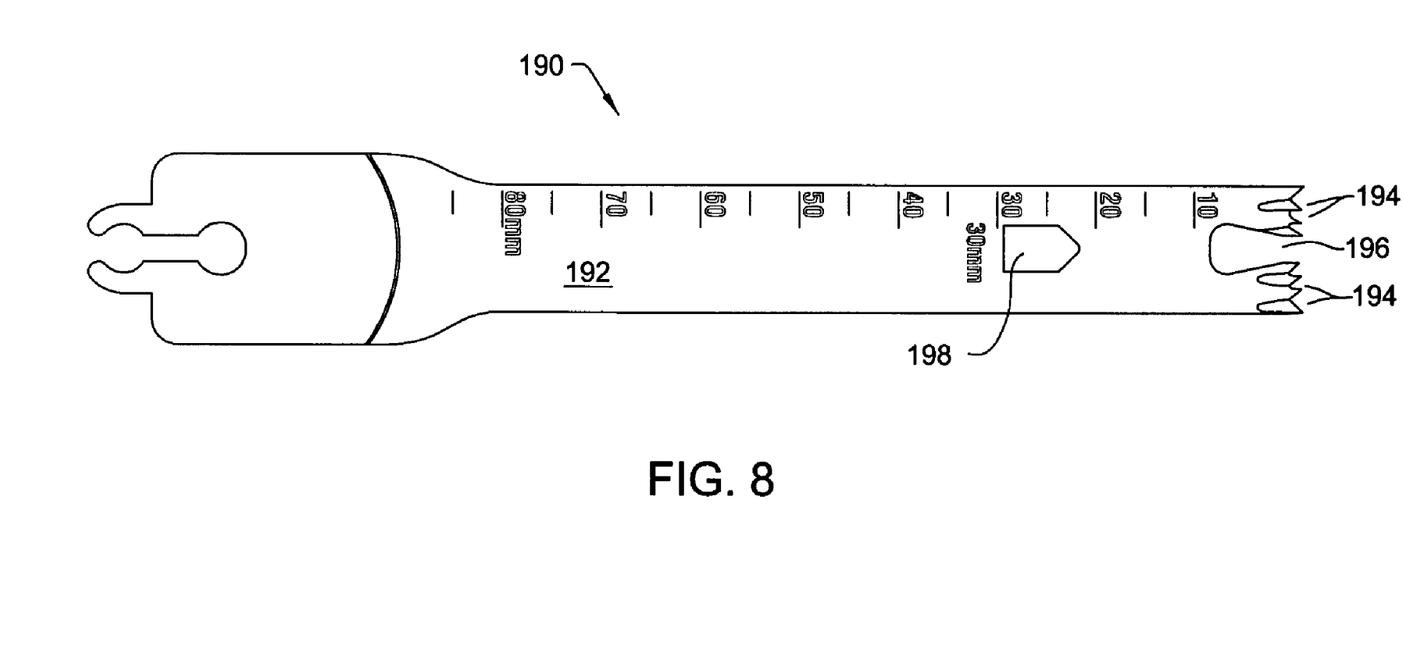
FIG. 8 is a plan view of a fourth alternative sagittal saw blade constructed in accordance with this invention.

FIG. 8 illustrates still another sagittal saw blade 190 constructed in accordance with this invention. Blade 190 has a body 192 from which teeth 194 extend distally forward. Blade 190 is formed so that the tips of teeth 194 are on a common curve that extends inwardly toward the proximal end of the blade. An opening 196 extends proximally rearward between the teeth 194. Blade body 192 is formed so that opening 196 is centered along the longitudinal axis of the blade 190. The blade body is shaped so that extending rearwardly from teeth 194, opening 196 increases in width.

Blade body 192 is further formed to define a void space 198. As seen in FIG. 8, blade body 192 is shaped so that void space 198 is spaced proximally away from opening 196. Blade body 192 is formed so that distal end edge of void space 198 has a triangular shape such that most distal point of the edge is located along the longitudinal axis of the blade. On either side of the point, the edge extends proximally rearward. Blade body 192 is further formed so that void space 198 has two parallel side edges and proximal end edge. The side edges are parallel to the blade longitudinal axis. The proximal end edge of the void space 198 is perpendicular to the side edges. Void space 198 is provided to reduce the overall weight of blade 190.

Figure 9:
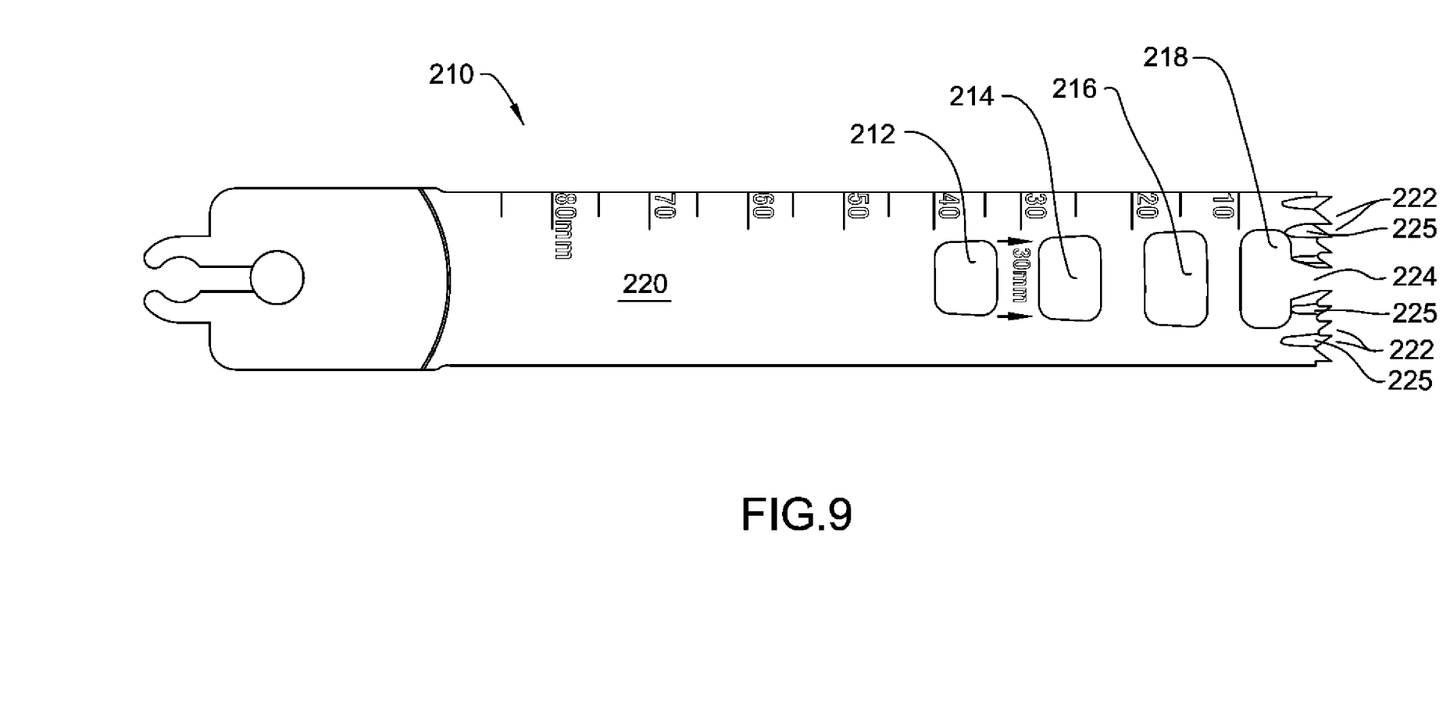
FIG. 9 is a plan view of a fifth alternative sagittal saw blade constructed in accordance with this invention.

FIG. 9 illustrates an alternative sagittal saw blade 210 of this invention formed with four void spaces 212, 214, 216 and 218. Blade 210 has a blade body 220. Teeth 222 extend forward from the distal front end of the blade body 220. Blade 210 is formed with an opening 224 located between teeth 222 that extends proximally rearward. On either side of opening 224, blade 210 is further formed so that there are a plurality of spaced apart dubs 225 in the teeth. These include, on each side of opening 224, at least one dub 225 that is laterally spaced away from opening 224. Opening 224 is centered on the longitudinal center line of the blade 210. Blade body 220 is shaped so that, extending proximally rearward, the width of opening 224 increases.

Opening 224 opens into the distally located void space, void space 218. The blade 210 is formed so void space 218 has a length perpendicular to the longitudinal axis of the blade that is at least equal to the combined width of opening 224 and a plurality of teeth 22 on the opposed sides of the opening. The length of void space 218 is such that on each side of opening 224 at least one of the proximally extending dubs 225 that is spaced away from opening 224 opening into void space 218. Blade 210 is formed so that the four void spaces 212, 214, 216 and 218 are spaced apart from each longitudinally along the blade body 220. Each of the void spaces 212-218, like opening 224 is centered along the longitudinal axis of the blade 210. The blade body 220 is shaped so that the, extending rearwardly from the distal end of the blade, the side edges of the void spaces taper inwardly. Thus, for each void space 212, 214, 216 and 218, the proximal end edge of the space is shorter than the complementary distal end edge. The distal end edge of void space 212 is shorter than the adjacent proximal end edge of void space 214. The distal end edge of void space 214 is shorter than the adjacent proximal end edge of void space 216. Similarly, the distal end edge of void space 216 is shorter than the adjacent proximal end edge of void space 218.

In the illustrated version of the invention, the side edges of the void spaces 212-218 on each side of the blade are linearly aligned. Further, the corners of the void spaces 216-218 are rounded. Openings 212, 214, 216 serve to reduce the overall weight of the blade. Openings 212, 214, 216 also facilitate the line-of-sight positioning of blade 210 during cutting.

Figure 10:
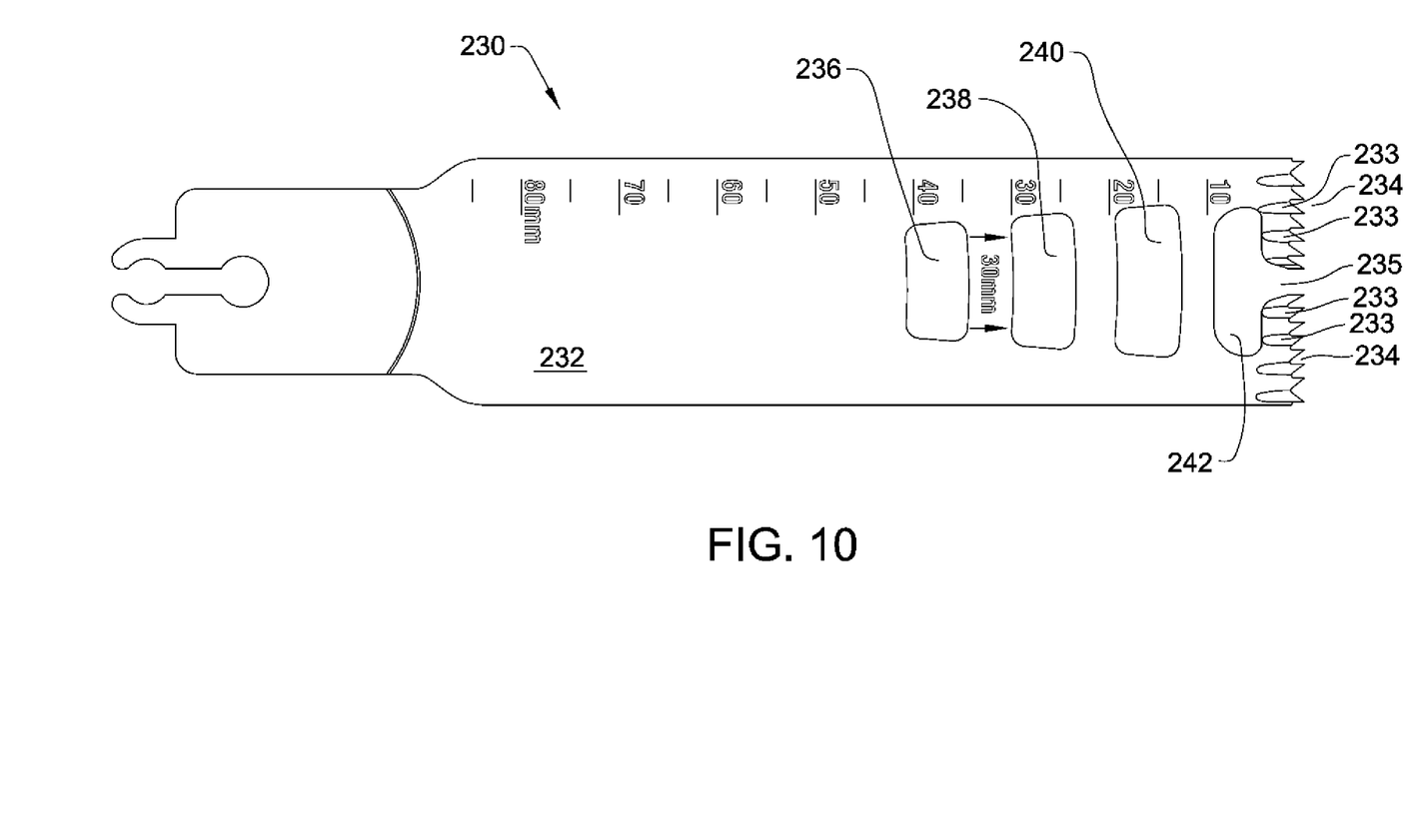
FIG. 10 is a plan view of a sixth alternative sagittal saw blade constructed in accordance with this invention.

Blade 230 of FIG. 10 is a variation of blade 210. Initially it is note that width of blade 230 is greater that the width of blade 210. Thus, it should be recognized that the features of this invention are independent of blade width. Blade 230 has a body 232 from which teeth 234 extend distally forward. Since blade body 232 is wider than blade body 220, blade 230 has more teeth 234 than blade 210. Blade body 230 is formed with an opening 235 similar in geometry to opening 224. Blade 230 is further formed so that on either side of opening 235 a number of proximally extending dubs 233, that are longitudinally spaced apart from each other, are formed in teeth 234. On each side of opening 235 there are plural dubs 233 that are longitudinally spaced from the opening.

Blade body 232 is formed so as to have four longitudinally spaced apart void spaces 236, 238, 240 and 242. Void space 242, the most distal of the void spaces, is the void space into which opening 235 opens. Blade body 232 is formed so that void space 242 has a geometry similar to that of void space 48 of blade 20 (FIG. 1). Void space 242 thus has a length in the direction perpendicular to the longitudinal axis of blade 230 that is at least equal to the combined widths of opening 235 and a plurality of teeth 234 on opposed sides of the opening. Void space 242 actually has a width such that, on each side of opening 235 plural dubs 233 that are spaced apart from the opening open into void space 242. Void spaces 236, 238 and 240 correspond generally to void spaces 212, 214 and 216, respectively, of blade 210. Thus void spaces 236, 238, and 240 have the same relative widths as void spaces 212, 214 and 216. One difference between blades 210 and 230 is that the proximal and distal edges of void spaces 236, 238 and 240 are not straight, they are curved. More specifically, blade body 232 is formed so that the edges of the body that define the proximal and distal ends of void spaces 236, 238 and 240 curve distally forward. Each of these curved edges is centered on the longitudinal center line of the blade. Openings 236, 238 and 240 reduce the overall weight of blade 230.

From the above description it should be clear that there is no requirement that all versions of the invention incorporate all features of the inventive blades of this invention. Thus, there is no requirement all sagittal saw blades of this invention have both inwardly recessed teeth and one or more chip catchments.

Similarly, the geometries of alternative versions of this invention may vary from what has been illustrated. For example, in the described version of the invention, with regard to blade 20, teeth 28 are positioned so that all the teeth points are on a single curve plot. In an alternative version of the invention, the teeth may be arranged so that teeth points 42a, b, . . . and h are on a first common curve and points 42i, j, . . . and p are on a second common curve separate from the first curve. In still other versions of the invention, the plots on which teeth points 42 lie may not be a curve, the plot may be linear. In other version of the invention the teeth on each side of the blade may be inwardly stepped. For example, on one side of the blade the teeth 28 are arranged so that teeth 42a, b and c are a first common distance from the proximal end of the blade; teeth 42d, e and f are a second common distal from the proximal end that is less than the first common distance; and teeth 42g and h are the third distance from the proximal end that is less than the second distance.

Also. the teeth on each side of the blade may be different plots. Thus, the outer teeth 28 forming points 42a through d and 42i through l are on a first plot. The remaining inner teeth forming points 42e through h and 42m through p are on a second plot that is proximal, inwardly recessed, relative to the first plot. For example in one version of the invention, the outer teeth may be on a common on separate convex plots, the inner teeth may be on separate or a common concave plots. Alternatively, one or both of these individual plots are linear.

Figure 11:
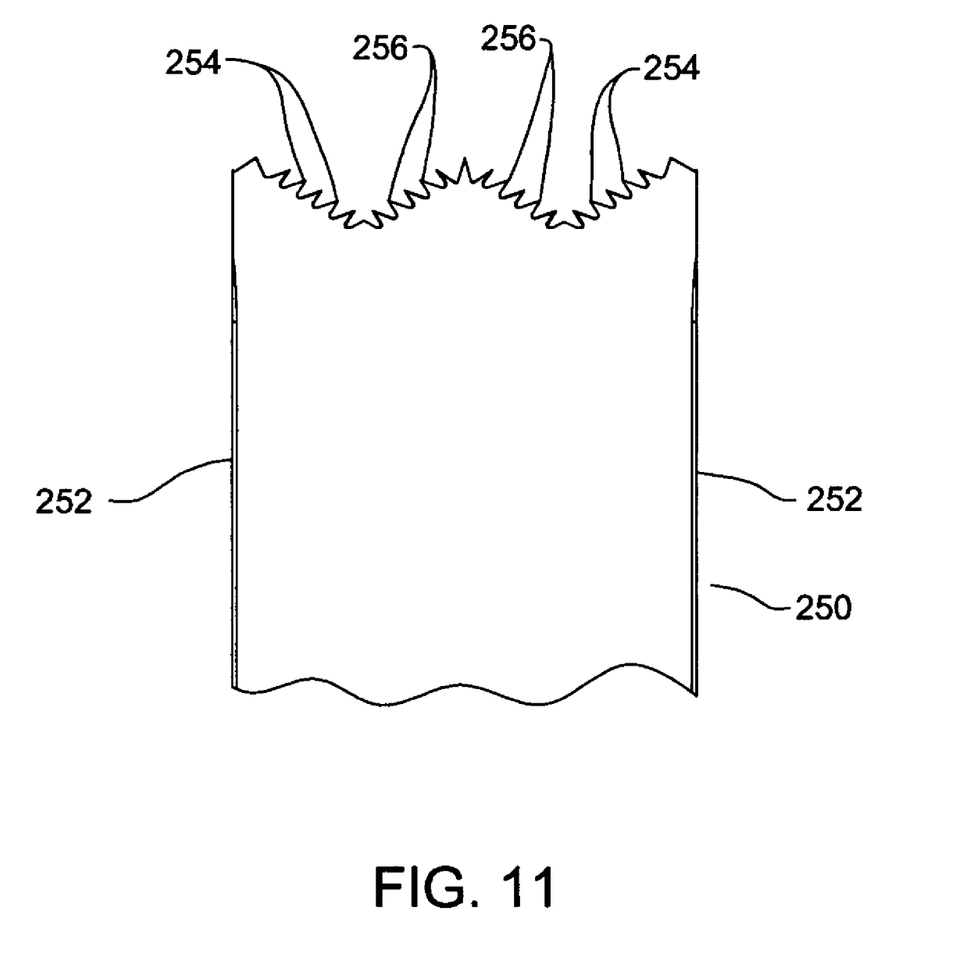
FIG. 11 is a plan view of the distal end of a seventh alternative sagittal saw blade constructed in accordance with this invention.

FIG. 11 illustrates still another variation of how the teeth of a sagittal saw may be arranged according to this invention. Here the distal end of a blade 250 is illustrated. Extending inwardly from the opposed sides 252 of the blade 250 there are a plurality of teeth 254 arranged so that, going inward from the side, the more inner teeth are closer to the proximal end of the blade. Adjacent each most proximal located tooth 254, on each side of the blade 250 there are a plurality of teeth 256. On each side of the blade, relative to the longitudinal axis, each tooth 256 is closer to the axis is spaced further from the proximal end than the adjacent tooth spaced further from this axis. Thus, in some versions of this embodiment of the invention, there may be three or more spaced apart teeth that are spaced apart a common distance from the blade proximal end that are the most distally located teeth.

Further there is no requirement that in all versions of the invention, the tooth pattern by symmetric relative to the longitudinal axis of the blade of the sagittal saw blade of this invention. In some versions of this invention, only the teeth located on one side of the distal end of the blade may be recessed proximally relative to the adjacent teeth. In these versions of the invention asymmetrically located holes may be formed in the blade body to minimize vibrations caused by unequal loading.

Also, the geometries of the void spaces that function as bone chip catchments may vary. Similarly, there is no requirement that the webs that extend through these void spaces be coplanar with the center planes of the blade bodies with which these webs are integral. Clearly, other blades than the illustrated blades may be formed with the slots that open into the void space. In some versions of the invention, one or more these slots may substitute for the front end opening into the void space. Thus in some versions of the invention, a slot may extend from the spaced between each pair of opposed teeth rake surfaces into the void space.

It should likewise be recognized that the relative orientations of the teeth of the blades of this invention need not be as described. In some versions of the invention, each tooth of a blade of this may have a common geometry and/or a common orientation.

Furthermore, it should be clear that the method from which the blade teeth are formed does not limit the scope of this invention. Grinding, laser cutting and/or compress tooth set processes may be used to form the teeth of the saw blade of this invention.

It should likewise be appreciated that it may be desirable in alternative versions of the invention to form the blade so that plural discharge slots extend away from the void space that functions as the chip catchment.

Similarly, there is no requirement that in all versions of this invention the opening into the void spaces that function as the catchments be centered along the longitudinal axes of the blades of this invention. In some versions of this invention, the opening is offset from this axis. Further, in some versions of the invention, there may be two or more openings into these void spaces. In these versions of the inventions webs that extend across the openings hold the teeth that separate the openings from each other to the rest of the blade body.

Likewise alternative versions of the reciprocating/sternum saw of this invention are also possible. There is no requirement the saw teeth always be arranged in linear plots. In alternative versions of the invention, the saw teeth may be in a curved profile. Such curve can be concave. In other alternative versions of the invention, the teeth are arranged in stepped profile. Thus two or more adjacent teeth may be positioned such that their teeth are on a line that is parallel to the longitudinal axis through the blade body. Further the teeth of the blade may alternatively be positioned relative to each other so that the teeth tips are on a wave shape curve similar to the curve along which the teeth 254 and 256 of saw blade 250 of FIG. 11 lie.

Also, it may be desirable to form the reciprocating saw blade of this invention with slots between the adjacent teeth that extend to the opposed sides of the blade. These slots function as discharge conduits through which bone chips are ejected away from the bone blade teeth interface.

Thus, it is an object of the appended claims to cover all such variations and modifications that come within the true spirit and scope of this invention.

What is claimed is:

1. A surgical saw blade comprising:
 a planar blade body, said blade body shaped to have opposed proximal and distal ends and a longitudinal axis that extends between the ends;
 geometric features integral with the proximal end of said blade body to couple said blade body to a drive head so that said drive head can oscillate the blade body so that the distal end pivots relative to the proximal end; and
 a plurality of teeth that extend forward from the distal end of the blade body,
 wherein said blade body is further formed to define two spaced apart tines that extend proximally from the blade body distal end, said tines spaced symmetrically from the blade body longitudinal axis, said tines having distal ends that collectively form the distal end of said blade body wherein at least two said teeth extend forward from each said tine, said tines being collectively shaped to define an opening located between the distal ends of said tines that has a width perpendicular to the blade body longitudinal axis and a void space that is proximal to the opening between the distal ends of said tines and proximal to where said teeth extend forward from said tines, the void space extending through said blade body and being contiguous with the opening between the distal ends of said tines and having a width perpendicular to the blade body longitudinal axis that is greater than the width of the opening between the distal ends of said tines.

2. The surgical saw blade of FIG. 1, wherein:
 each said tooth has a width; and
 said tines are further formed so that the void space proximal to the opening between the distal ends of said tines has a width at least equal to the width of the opening between the distal ends of said tines and the width of two teeth on each side of the opening between the distal ends of said tines.

3. The surgical saw blade of claim 1, wherein each said tine is further formed to have at least one groove, the groove extending proximally from the distal end of the tine, being spaced away from the opening between the distal ends of said tines, and extending along said tine to the void space.

4. The surgical saw blade of claim 1, wherein said teeth are arranged so that on each said tine at least one tooth is spaced forward from an adjacent tooth on said tine that is located closer to the opening between the distal ends of said tines.

5. The surgical saw blade of claim 1, wherein, on each said tine, said teeth are arranged so that each tooth is located proximal to the adjacent tooth that is spaced further from the opening between the distal ends of said tines.

6. The surgical saw blade of claim 1, wherein:
 the void space defined by said tines into which the opening between the distal ends of said tines opens is a first void space;
 said blade body is further formed to have a second void space that is spaced away from and located proximal to the first void space; and
 said blade body is further formed to have a recess that extends inwardly from an outer surface of the blade body, the recess extending from the first void space to the second void space.

7. The surgical saw blade of claim 1, wherein said blade body is further formed to have a slot that extends inwardly from a face surface of the body, said slot extending from the void space to a side edge of the blade body.

8. The surgical saw blade of claim 1, wherein, on each said tine, said teeth are arranged so that:

there is an outer tooth that is spaced furthest from the opening between the distal ends of said tines and a plurality of additional teeth that extend forward from between the outer teeth and the opening between the distal ends of said tines and each said tooth has an orientation; and the outer tooth has an orientation that is different from the orientation of the plurality of additional teeth.

9. The surgical saw blade of claim 1, wherein the geometric features integral with the proximal end of the blade body to couple the blade body to a drive head include an opening formed in the proximal end of the blade body that is located along the longitudinal axis of the blade body.

10. A surgical saw blade, said saw blade including:

a planar body having opposed proximal and distal ends and a longitudinal axis that extends between the ends;

geometric features integral with the proximal end of said blade body to couple said blade body to a drive head so that said drive head can oscillate the blade body so that the distal end pivots relative to the proximal end;

tines formed in said blade body that are located forward of the proximal end, each tine having a distal end, the distal ends of said tines collectively forming the blade body distal end, said tines being formed in said blade body so as to be spaced apart from each other around the blade body longitudinal axis so as to define an opening between the distal ends of said tines that has a width perpendicular to the blade body longitudinal axis and a void space that extends through said blade body that is contiguous with and proximal to the opening, the void space having a width perpendicular to the blade body longitudinal axis, the width of the void space being greater than the width of the opening between the distal ends of said tines; and a plurality of laterally spaced apart teeth that extend forward from each said tine, said teeth being arranged so that on each said tine there is at least one tooth close to the opening between the distal ends of said tines and an adjacent tooth located further from the opening, the adjacent tooth being spaced forward of the tooth located close to the opening between the distal ends of said tines.

11. The surgical saw blade of claim 10, wherein each said tine is further formed to have at least one groove, the groove extending from the tine distal end, being spaced from the opening between the distal ends of said tines, and extending to the void space.

12. The surgical saw blade of claim 10, wherein, on each said tine, said teeth are further arranged so that, each tooth is spaced distally forward from the adjacent tooth located closer to the opening between the distal ends of said tines.

13. The surgical saw blade of claim 10, wherein, on each said tine, said teeth are arranged so that:

there is an outer tooth spaced furthest from the opening between the distal ends of said tines and a plurality of additional teeth that extend forward from the tine between the outer tooth and the opening between the distal ends of said tines and each said tooth has an orientation; and the outer tooth has an orientation that is different from the orientation of the plurality of additional teeth.

14. The surgical saw blade of claim 10, wherein:

said blade body, including said tines, have a thickness; and a web extends between said tines across the void space between said tines, the web having a thickness less than the thickness of said tines.

15. A surgical saw blade, said saw blade including:

a planar body having opposed proximal and distal ends and a longitudinal axis that extends between the ends;

geometric features integral with the proximal end of said blade body to couple said blade body to a drive head so that said drive head can oscillate the blade body so that the distal end pivots relative to the proximal end;

tines formed in said blade body that are located forward of the proximal end, each tine having a distal end, the distal ends of said tines collectively forming the blade body distal end, said tines being formed in said blade body so as to be spaced apart from each other around the blade body longitudinal axis so as to define an opening between the distal ends of said tines that has a width perpendicular to the blade body longitudinal axis and a void space that extends through said blade body that is contiguous with and proximal to the opening between the distal ends of said tines, the void space having a width perpendicular to the blade body longitudinal axis, the width of the void space being greater than the width of the opening between the distal ends of said tines; and a plurality of teeth that extend forward from the distal end of each said tine, wherein each said tine is further formed to have at least one groove that is located inwardly from an outer surface of said tine and extends proximally from the distal end of said tine, is spaced away from the opening between the distal ends of said tines, and extends into the void space.

16. The surgical saw blade of claim 15, wherein, on each said tine, said teeth are arranged so that the at least one tooth is located forward from an adjacent tooth on said tine that is located closer to the opening between the distal ends of said tines.

17. The surgical saw blade of claim 15, wherein, on each said tine, said teeth are arranged so that each tooth is spaced distally forward from an adjacent tooth that is located closer to the opening between the distal ends of said tines.

18. The surgical saw blade of claim 15, wherein, on each said tine, said teeth are arranged so that:

there is an outer tooth spaced furthest from the opening between the distal ends of said tines and a plurality of additional teeth the extend forward from said tine between the outer tooth and the void space between the distal ends of said tines and each said tooth has an orientation;

the outer tooth has an orientation that is reverse relative to the orientation of the plurality of additional teeth; and said teeth are arranged on said tine so that the outer tooth is spaced distally forward from the plurality of additional teeth.

19. The surgical saw blade of claim 15, wherein on each said tine said teeth are arranged so that:

there is an outer tooth spaced furthest from the opening between the distal ends of said tines and a plurality of additional teeth the extend forward from said tine between the outer tooth and the void space between the distal ends of said tines, the additional teeth including an inner tooth that is located closest to the opening and each said tooth has an orientation;

the outer tooth has an orientation that is reverse relative to the orientation of tips of the plurality of additional teeth; and said teeth are arranged on said tine so that: the outer tooth is spaced distally forward from the additional teeth; and the inner tooth is spaced proximally rearward relative to the rest of said teeth on said tine.

20. The surgical saw blade of claim 15, wherein each said tine has opposed outer surfaces and at least one groove is formed on each outer surface of said tine.

* * * * *